(12) United States Patent
Krasikoff et al.

(10) Patent No.: US 8,845,608 B2
(45) Date of Patent: Sep. 30, 2014

(54) HOLSTER-STYLE POUCH ASSEMBLY FOR CARRYING A POST-SURGICAL FLUID DRAINAGE CONTAINER

(71) Applicant: ELN Group, LLC, Cary, IL (US)

(72) Inventors: Nina Krasikoff, Chicago, IL (US);
Laurine Sargent, Chicago, IL (US);
Eric Ladewig, Cary, IL (US)

(73) Assignee: ELN Group, LLC, Chicago, IL (US)

( * ) Notice: Subject to any disclaimer, the term of this patent is extended or adjusted under 35 U.S.C. 154(b) by 0 days.

(21) Appl. No.: 13/791,770

(22) Filed: Mar. 8, 2013

(65) Prior Publication Data

US 2013/0245584 A1    Sep. 19, 2013

Related U.S. Application Data

(60) Provisional application No. 61/608,502, filed on Mar. 8, 2012.

(51) Int. Cl.
*A61F 5/44* (2006.01)
*A61M 27/00* (2006.01)

(52) U.S. Cl.
CPC .............. *A61F 5/4408* (2013.01); *A61M 27/00* (2013.01)
USPC .......................................... 604/345; 604/353

(58) Field of Classification Search
CPC .......... A61F 5/44; A61F 5/4408; A61F 5/449
USPC .................. 604/327–331, 174, 179, 345, 353
See application file for complete search history.

(56) References Cited

U.S. PATENT DOCUMENTS

| 5,234,420 | A | * | 8/1993 | Horton et al. | 604/345 |
| 5,496,282 | A | * | 3/1996 | Militzer et al. | 604/179 |
| 2008/0188822 | A1 | * | 8/2008 | Lodge et al. | 604/385.03 |
| 2008/0312615 | A1 | * | 12/2008 | Hunter | 604/345 |
| 2012/0091181 | A1 | * | 4/2012 | Barnes | 224/600 |

* cited by examiner

*Primary Examiner* — Philip R Wiest
*Assistant Examiner* — Benjamin Klein
(74) *Attorney, Agent, or Firm* — Tracy Jong Law Firm; Tracy P. Jong; Cheng Ning Jong

(57) ABSTRACT

A holster-style pouch assembly carries a post-surgical fluid drainage system. The assembly includes an adjustable waistband, a pouch and a loop band. The pouch has an upwardly extending flap for at least partially closing off the pouch interior from the exterior environment. The flap has closure mechanisms attachable to and detachable from closure mechanisms disposed on the pouch interior and exterior. The flap extends over the waistband such that the pouch is suspended and secured with fastening mechanisms to the waistband when the flap closure mechanisms and the pouch closure mechanisms are attached. The pouch is capable of containing at least one post-surgical fluid drainage container. In operation, one or more fluid drainage tubes is capable of extending downwardly into the fluid drainage collection container inside the pouch. The fluid drainage tube is securable between the waistband and the loop band when the band closure mechanisms are attached.

8 Claims, 3 Drawing Sheets

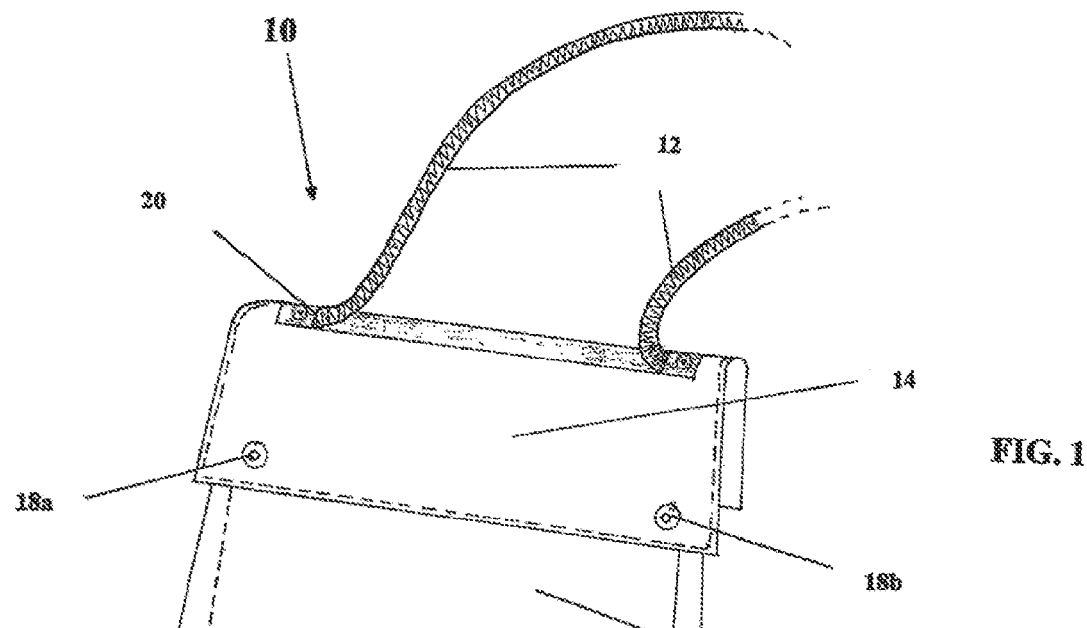
FIG. 1
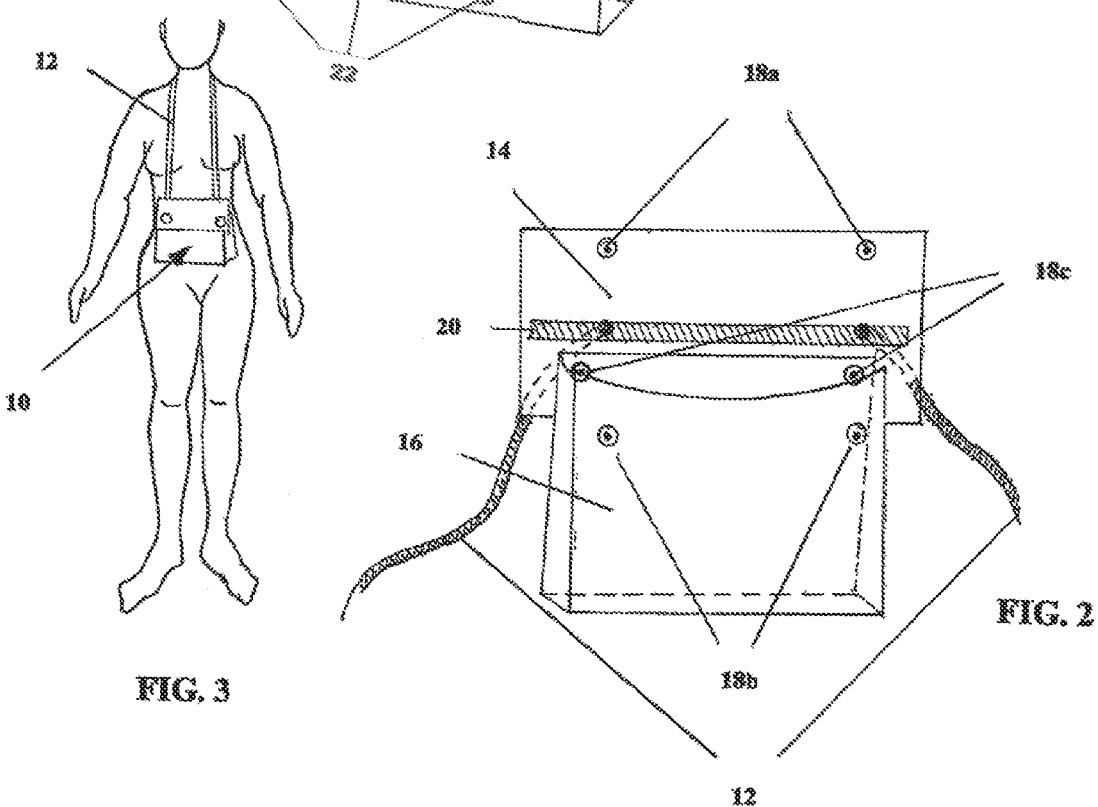
FIG. 3
FIG. 2

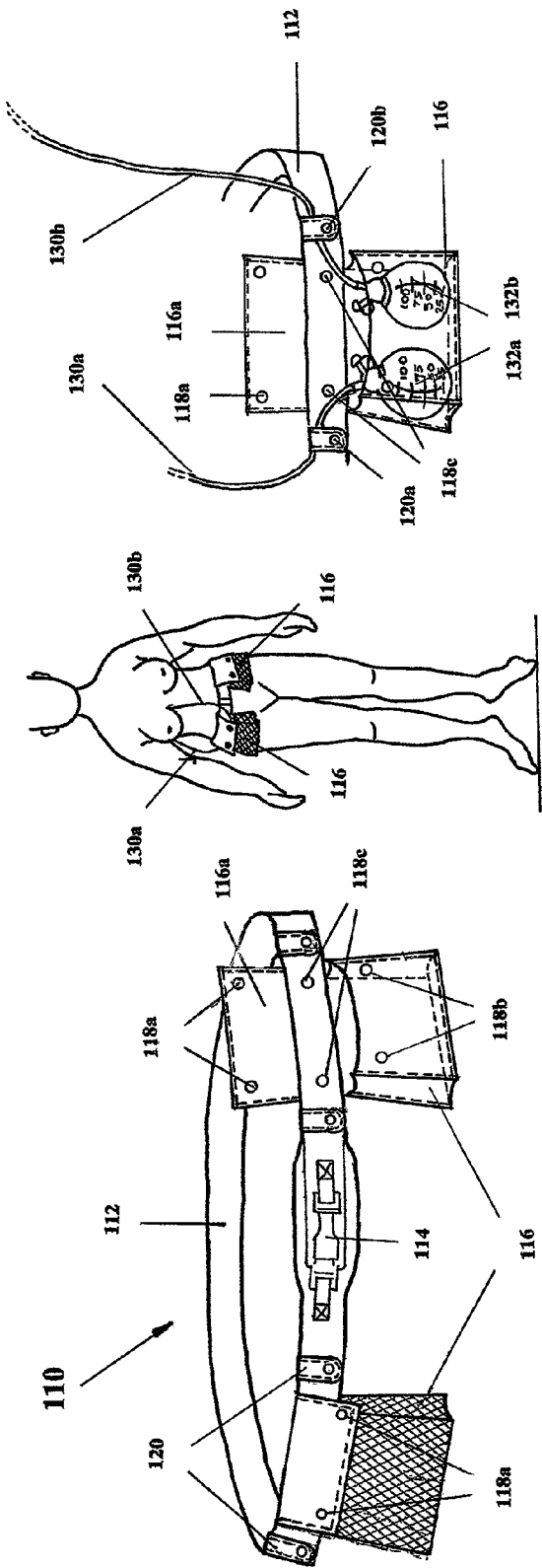
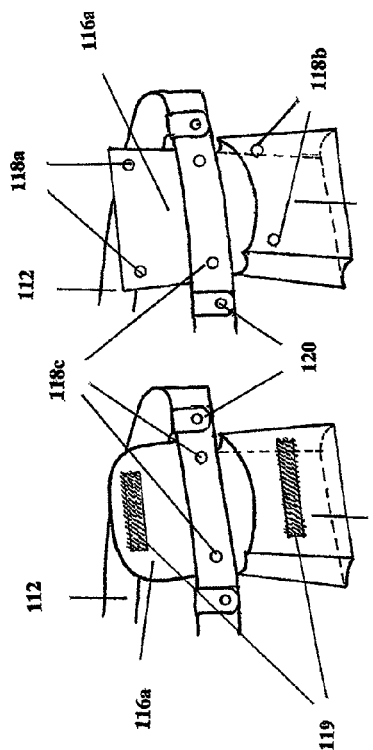

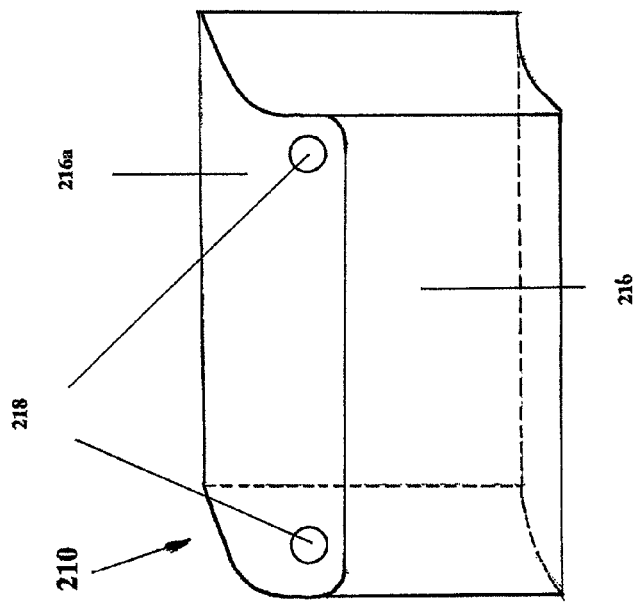
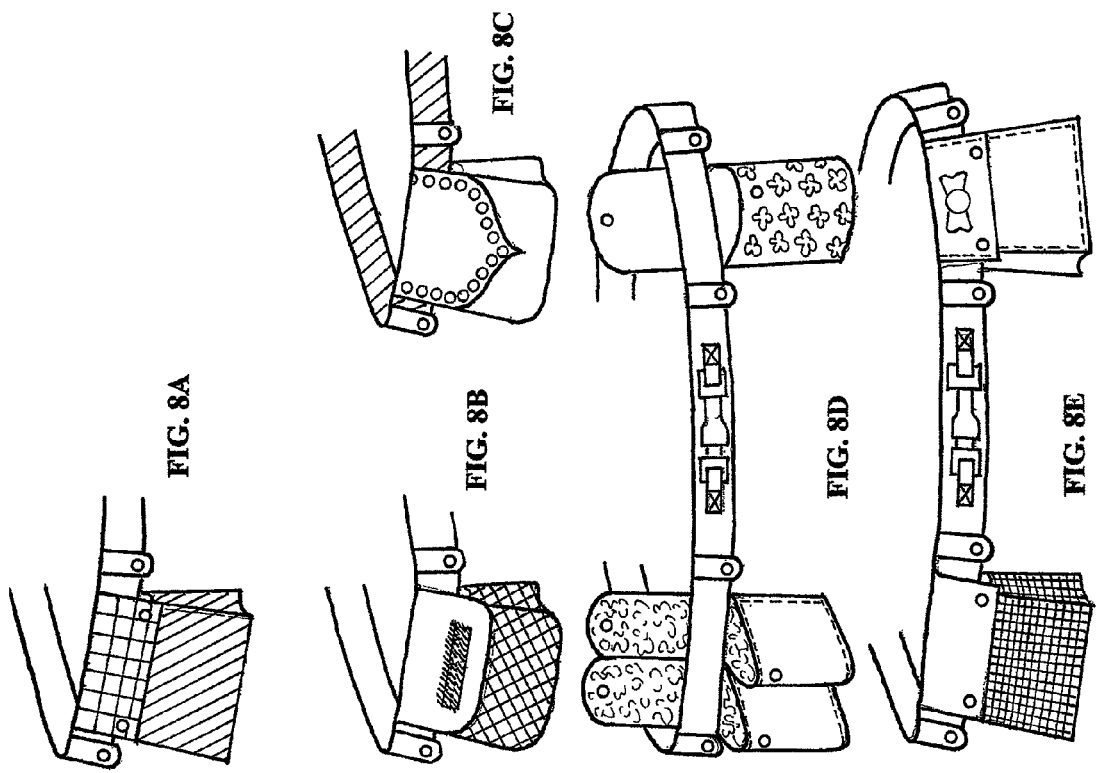

HOLSTER-STYLE POUCH ASSEMBLY FOR CARRYING A POST-SURGICAL FLUID DRAINAGE CONTAINER

CROSS-REFERENCE TO RELATED APPLICATION(S)

This application is related to and claims priority benefits U.S. Provisional Patent Application Ser. No. 61/608,502 filed on Mar. 8, 2012, entitled "Holster-Type Pouch Assembly For Carrying A Post-Surgical Fluid Drainage Container". The '502 provisional application is hereby incorporated by reference herein in its entirety.

FIELD OF THE INVENTION

The present invention relates to medical devices and, more particularly, to a holster-style pouch assembly for securely carrying one or more post-surgical fluid drainage collection containers into which tubes carrying post-surgical fluid extend

BACKGROUND OF THE INVENTION

Post-surgical drainage systems are generally needed following abdominal, breast mastectomy and thoracic surgeries. One or more surgical drains are typically placed near the surgical incisions. Although these drains can be uncomfortable and inconvenient, they are usually medically necessary. Surgical drains prevent blood and fluid buildup under the skin, and encourage healing and recovery. Daily measuring of fluids and keeping the collection containers, referred to herein as "surgical drains" clean and clear will aid in preventing infections. The collection containers, surgical flasks or surgical drains often have volumetric fluid measurement markings on their outside.

A surgical drain system includes fluid drainage tubing, fluid collection drains, and sometimes a measuring cup. The main purpose of the surgical drain system is to enable fluid elimination and collection from the body. The fluid drainage tubes extend from the patient under the skin near the incision. Fluid drainage tubes are usually held in place with sutures so that the tube does not slip out of the incision accidentally and cause a leak. The current commercially available designs do not provide the type of support or security needed to keep the surgical drainage system in place.

The current commercially available design is apron-style with slits to contain surgical drains made from a solid and non-breathable nylon, which results in sweating and unhygienic conditions. The current design also has hard-to-manage clasps located on the back of the apron, which is of questionable usefulness due to the limited range of motion of a post-surgical patient. The present Holster Belt System overcomes many of the impediments of the current commercially available design.

Post-surgical camisoles or vests are bulky and unattractive, with the pockets for the surgical drains located inside wide and oversized clothing, which results in pain from the moving and bouncing of the drains throughout the day. These camisole and vest designs are therefore problematic because the process of post-surgical healing can last for weeks. Camisole and vest designs are also disadvantageous because of the difficulty in viewing fluid collection in the surgical drains and to maintain hygiene. The design also requires the patient to purchase several such camisoles or vests to maintain hygiene and to accommodate different climates.

The foregoing prior solutions fail to provide stable, comfortable, painless and hygienic design and do not satisfy the requirements of proper post-surgical healing.

The present Holster Belt System offers patients a unique and effective option compared to existing commercially available surgical fluid drainage systems. The present Holster Belt System (HBS) is designed to support wearing of a surgical drain system and eliminate an outdated option of pinning tags or loops, which are located on the top or sides of the surgical drains, to undergarments or clothing. The HBS is designed to assist during the difficult time of recovery with comfort and fashionable design features. The present design overcomes shortcomings and inefficiencies in current surgical drain systems, which are bulky, clumsy and handicapping, and which provides little of no support and cause pain to the patients due to unstable position of pinning tubes and surgical drains.

SUMMARY OF THE INVENTION

In one embodiment, a holster-style pouch assembly for carrying a post-surgical fluid drainage system comprises:
    an adjustable waistband having a buckle for removably securing the waistband around a patient's abdomen;
    a pouch having an upwardly extending flap for at least partially closing off the pouch interior from the exterior environment, the flap having at least one closure mechanisms attachable to and detachable from at least one closure mechanisms disposed on the pouch exterior, the flap extendable around the waistband such that the pouch is suspended and secured to the waistband when the at least one flap closure mechanism and the at least one pouch closure mechanism are attached, the pouch capable of containing at least one post-surgical drain;
    at least one loop band having a closure mechanism attachable and detachable from the waistband.

In operation, at least one fluid drainage tube is capable of extending downwardly into the fluid drainage collection container inside the pouch. The at least one fluid drainage tube is securable between the waistband and the at least one loop band when the band closure mechanism is attached to the waistband.

In a preferred pouch assembly embodiment, the waistband and the at least one loop band each has a bottom edge. The at least one loop band further has a pair of attachable and detachable closure mechanisms located at the loop bottom edge. The pair of closure mechanisms is readily attachable and detachable from the waistband bottom edge. Each of the at least one loop bands is attachable to the waistband bottom edge when the band closure mechanisms are attached.

In a preferred pouch assembly embodiment, at least one fluid drainage tube is capable of extending downwardly into the surgical drains or bulbs inside the pouch. The at least one fluid drainage tube is securable between the waistband and the at least one loop band when the band closure mechanisms are attached to the waistband.

In a preferred pouch assembly embodiment, the at least one flap closure mechanism and the at least one pouch closure mechanism can comprise: (a) cooperating hook and loop fastening material, (b) press-fit fasteners, and/or (c) magnetic fasteners.

In one embodiment, a holster belt pouch assembly for carrying a post-surgical drainage system comprising:
    a waistband having a buckle for removably securing the waistband around a patient's abdomen;
    a plurality of pouches, each of the pouches having an upwardly extending flap for at least partially closing off the pouch interior from the exterior environment, the flap having at least one closure mechanism attachable to and detachable from at least one closure mechanism disposed on the pouch exterior, the flap extendable over the waistband such that the pouch is suspended and secured with fastening mechanisms to the waistband, from the waistband when the at least one flap closure mechanism and the at least one pouch closure mechanism are attached, the pouch capable of containing at least one post-surgical fluid drainage collection container;

at least one loop band having a closure mechanism attachable and detachable from the waistband.

In operation, at least one fluid drainage tube is capable of extending downwardly into the fluid drainage collection container inside the pouch. The at least one fluid drainage tube is securable between the waistband and the at least one loop band when the band closure mechanism is attached to the waistband.

In one embodiment, a protective shower bag comprises:
a pouch having front and back walls, a pair of oppositely disposed side walls interconnecting the front and back walls, and a bottom wall, the walls forming an interior pouch volume with a top opening, each of the front and back walls having a width;
at least one closure mechanism disposed on the exterior surface on each of the pouch front and back walls;
a detachable flap having an inside planar surface and an outside planar surface, the flap foldable such that in the folded position the flap has a ridge that substantially covers the pouch top opening, the flap having a width greater than each of the pouch front and back walls, the flap having at least one closure mechanism disposed on the flap inside surface on either side of the ridge;
a rigid reinforcing panel extending along the ridge on the interior surface of the flap;
a neck harness having two opposite ends, each of the ends attached to the reinforcing panel at opposite ends thereof.

In operation, attaching the flap closure mechanisms to the pouch closure mechanisms shields the pouch interior surface from the external environment when the neck harness is suspended from a patient's neck.

In a preferred protective shower bag embodiment, attaching the flap closure mechanisms to the pouch closure mechanisms shields the pouch interior surface from the external environment when the neck harness is suspended from a patient's neck.

In a preferred protective shower bag embodiment, the flap closure mechanisms and the pouch closure mechanisms comprise: (a) cooperating hook and loop fastening material, (b) press-fit fasteners, and/or (c) magnetic fasteners.

In a preferred protective shower bag embodiment, at least one of the pouch front, back and side walls has at least one opening formed therein for facilitating drainage of accumulated water from the inside pouch volume to the pouch exterior.

BRIEF DESCRIPTION OF THE DRAWING(S)

FIG. 1 is a front perspective view of a "Flop-Top" protective shower bag for use by post-surgical patients required to wear fluid collection drainage equipment.

FIG. 2 is a front perspective view of the "Flop-Top" protective shower bag of FIG. 1 with the top flap in the fully opened position.

FIG. 3 is a front view of a patient wearing the "flop-top" protective shower bag around the neck.

FIG. 4 is a front perspective view of the present Holster Belt System for holding and carrying a post-surgical drainage system.

FIG. 5 is a front view of a patient wearing the present Holster Belt System.

FIGS. 6A and 6B illustrate embodiments of fastening mechanisms that can be employed in the present Holster Belt System.

FIG. 7 is a perspective view of a portion of the present Holster Belt System with the flap in the fully open position having two surgical drains with volumetric markings for collecting and measuring the amount of fluid drained from the area of the patient that underwent surgery.

FIGS. 8A through 8E illustrate embodiments of fabrics, fasteners and decorative features that can be used with the pouch and flap portions of the present Holster Belt System.

FIG. 9 is a perspective view of a plastic pouch for containing and carrying the various components of the present Holster Belt System and accessories therefor.

DETAILED DESCRIPTION OF PREFERRED EMBODIMENT(S)

Referring first to FIG. 1, a "Flop-Top" protective shower bag 10 for use by post-surgical patients required to wear surgical drains. "Flop-Top" protective shower bag 10 includes a neck harness 12, a pouch 16 and a detachable flap 14. Flap 14 is fastened to pouch 16 by front external snaps 18a and 18b. Neck harness 12 is preferably made from a lightweight, fast-drying material, such as neoprene.

FIG. 2 shows the "Flop-Top" protective shower bag of FIG. 1 with top flap 14 in the fully opened position and showing a reinforcing panel 20 located along the ridge of flap 14. Flap 14 is fastened to pouch 16 by rear internal snaps 18c, providing additional support to flap 14 and pouch 16. Reinforced panel 20 prevents flap 14 from wrinkling or possibly collapsing due to exposure to warm water under pressure. At least one, and preferably three, spaced holes are formed on the bottom wall of the pouch to provide a drainage passage for water or condensation that may have entered the protective shower bag. As shown in FIG. 2, neck harness 12 extends through flap 14 and is attached at either side of reinforcing panel 20.

FIG. 3 is a front view of a patient wearing the "Flop-Top" protective shower bag 10 around the neck via harness 12.

As shown in FIGS. 1, 2, and 3, flap 14 of protective shower bag 10 is wider than the width of underlying pouch 16 to prevent water and soap from entering inside the pouch while the patient is showering.

In FIG. 4, the Holster Belt System 110 includes a waistband or belt 112, preferably formed from elastic or partially elastic material, and a buckle 114. Buckle 114 is preferably an adjustable luggage-style buckle that opens and closes easily and securely. Pouches 116 are fastened to waistband 112 by fastening mechanisms 118c, located on either side buckle 114. Flap 116a is closed on pouch 116 by fastening mechanisms 118a and 118b. Pouches 116 are preferably formed from lightweight, hygienic, disposable, biodegradable mesh material. Loop bands 120 are attached to top of waistband 112, direct and secure fluid drainage tubes (not shown) to waistband 112 as they extend into pouches 116.

FIGS. 6A and 6B show embodiments of fastening mechanisms that can be employed in the present Holster Belt System, shown pouches 116 shown with their flaps 116a. In FIG. 6A, flap 116a is fastened to the main portion of pouch 116 by cooperating hook-and-loop fastening material 119 (commercial brand VELCRO®). In FIG. 6B, flap 116a is fastened to the main portion of pouch 116 by snaps 118a and 118b. Flap 116a and pouch 116 are attached to waistband 112 by fastening mechanisms 118c. As in FIG. 4, loop bands 120 are attached to top of the waistband 112 and secure fluid drainage tubes (not shown) to waistband 112 as they extend into pouches 116.

FIG. 5 is a front view of a patient wearing the present Holster Belt System including pouches 116 with fluid drainage tubes 130a and 130b extending into pouches 116.

FIG. 7 is a perspective view of a portion of the present Holster Belt System with flap 116a in the fully open position. Flap 116a is fastened to the main portion of pouch 116 by snaps 118c, which secures pouch 116 to waistband 112. Flap 116a is attached to pouch 116 by fastening mechanisms 118a and 118b. Two collection containers or surgical flasks 132a and 132b with volumetric markings for collecting and measuring the amount of fluid drained via fluid drainage tubes 130a and 130b, respectively, from the area of the patient having undergone surgery. Flasks 132a and 132b are contained inside pouch 116.

FIGS. 8A through 8E illustrate embodiments of fabrics, fasteners and decorative features that can be used with the pouch and flap portions of the present Holster Belt System.

FIG. 9 is a perspective view of a plastic pouch 210 for containing and carrying the various components of the present Holster Belt System and accessories therefor. Pouch 210 includes a main portion 216 with a flap 216a that is fastened to pouch 216 by snaps 218. The most common accessories carried in plastic pouch 210 are bandages, such as, for example, a nipple tube bandage, a half-moon dome bandage, an absorptive skirt bandage, and an areola pad bandage.

Pouches 116 and flaps 116a are attached to the waistband with press-fit, fastening mechanisms or magnetic snaps 118c, thereby enabling easy access to measure and dispose fluids from surgical drain collection flasks. Magnetic snaps are preferably used for strength, ease and security to keep fluid drainage tubing in place.

The HBS has two pairs of narrow flat loop bands, shown in FIG. 4 as loop bands 120, positioned on either side of the pockets with magnetic or press-fit snaps used to direct and secure the fluid drainage tubing in a stable position close to the patient's body, and to direct and maintain the tubing in the pouches. These loops prevent from accidental tugging of the drains or tubing, which could cause leakage and unnecessary pain to the patient.

The HBS is an efficient, painless, hygienic and fashionable design that provides comfort and stability through the duration of a patient's time wearing the surgical drain system. The HBS helps the patient stay in control of the fluid drainage process and provides a clear view of surgical drain system while measuring fluids, exchanging pockets for hygienic reason and/or replacing the HBS with a plastic protective shower bag.

Centrally located on the front of the HBS is a convenient and easy-to-use buckle, which helps the patient to manage independently to buckle or unbuckle the HBS from the waist. Independent management of the device is important because mobility of a post-surgical patient can be excruciatingly limited during the post-surgical period. The HBS enables patients to resume daily activity with dignity and comfort.

The present HBS system is designed to nest surgical fluid drainage collection flasks in mesh pouches located on either side of the buckle of a belt style waistband. Each pouch can accommodate one or two collection drains, thereby allowing the patient freedom of movement and security without interrupting the purpose of the drains to continuously collect body fluids and aid in the post-surgical healing process. Light weight, hygienic mesh pouches, preferably constructed from stretchable mesh fabric, providing control and clear view of the fluid drainage tubes and surgical fluid drainage flasks, while post-surgical body fluids are being collected. Forming the pouches from lightweight and breathable fabric will provide comfort and avoid sweating from close contact of the pockets to the body for extended periods of time.

The present Holster Belt System accommodates various climates and can be multi-sized to provide personalized comfort and fit. The HBS is adjustable, hygienic, preferably, interchangeable, washable, disposable and biodegradable. The HBS provides clear and easy access to measure the collection of fluids, and can be worn under a patient's everyday clothing, which provides the freedom and privacy to resume daily activity with dignity and comfort throughout the various seasons of the year. The HBS allows patients resuming regular daily activities and provides security keeping the surgical drain system intact.

Suitable materials for the pockets can be one of more of nylon, spandex, cotton, micro-fiber elastic, elastene, neoprene, power-net fabrics, or combinations thereof, which are washable, hygienic and designed to ease the wearing of post-surgical drains.

The HBS buckle, centrally located on the front of the waistband, opens and closes with ease, thereby avoiding unnecessarily painful movements. This is particularly important to patients who have limited range of motion following surgery. The HBS is also designed to disguise bulkiness of the surgical fluid drainage system.

The HBS can be offered together with the protective shower bag shown in FIGS. 1-3, which is worn over the neck while showering. The hands-free protective shower bag concept provides the post-surgical patient with independence and privacy, and helps the patients to perform daily personal hygiene.

As stated previously, the HBS provides security, comfort, convenience and reduces bulkiness of carrying post-surgical fluid drains. The pouches evenly distribute the weight and size of the surgical fluid drainage containers across the waistband.

The HBS also addresses the psychological and emotional aspects of post-surgical recovery. The HBS is portable, less visible, comfortable and fashionable, which is important to patients recovering from highly invasive medical procedures. The HBS enables patients to resume daily activity with dignity, confidentiality and comfort, which fosters faster recovery.

The present HBS design will accommodate the most commonly used surgical fluid drainage systems, such as the system currently offered by Jackson-Pratt.

While particular elements, embodiments and applications of the present invention have been shown and described, it will be understood, of course, that the invention is not limited thereto since modifications can be made by those skilled in the art without departing from the scope of the present disclosure, particularly in light of the foregoing teachings.

What is claimed is:

1. A holster-style pouch assembly for carrying a post-surgical drainage system comprising:
    a waistband having a top edge, a bottom edge and a buckle for removably securing the waistband around a patient's abdomen;
    a pouch having oppositely disposed front and back walls, a pair of oppositely disposed side walls interconnecting said front and back walls and a bottom wall, said walls forming a pouch interior, an upwardly extending flap from a portion of said top edge for at least partially closing off said pouch interior from the exterior environment and leaving a space defined by said flap, said pouch interior and said waistband, said flap having at least two closure mechanisms attachable to and detachable from at least two closure mechanisms disposed on said pouch exterior, said flap extendable over said waistband such that said pouch is suspended from said bottom edge and secured with fastening mechanisms to said waistband, when said at least two flap closure mechanisms and said at least two pouch closure mechanisms are attached, said pouch capable of containing at least one post-surgical fluid drainage collection container;

at least two loop bands, at least one of said at least two loop bands is disposed on said waistband on a first side of said pouch and at least one of said at least two loop bands is disposed on said waistband on a second side of said pouch, said second side is oppositely disposed from said first side with respect to said pouch, each of said at least two loop bands includes a bottom edge and a pair of attachable and detachable closure mechanisms located at said loop band bottom edge, said pair of closure mechanisms readily attachable and detachable from said waistband bottom edge;

whereby at least one fluid drainage tube is capable of extending downwardly and channeled through the space into said fluid drainage collection container inside said pouch, said at least one fluid drainage tube securable between said waistband and at least one of said at least two loop bands when its corresponding loop band closure mechanism is attached to said waistband.

2. The pouch assembly of claim 1, wherein each of said at least two flap closure mechanisms and each of said at least two pouch closure mechanisms comprise cooperating hook and loop fastening material.

3. The pouch assembly of claim 1, wherein each of said at least two flap closure mechanisms and each of said at least two pouch closure mechanisms comprise press-fit fasteners.

4. The pouch assembly of claim 1, wherein each of said at least two flap closure mechanisms and said at least two pouch closure mechanisms comprise magnetic fasteners.

5. A holster belt pouch assembly for carrying a post-surgical drainage system comprising:

a waistband having a top edge, a bottom edge and a buckle for removably securing the waistband around a patient's abdomen;

a plurality of pouches, each of said pouches having oppositely disposed front and back walls, a pair of oppositely disposed side walls interconnecting said front and back walls and a bottom wall, said walls forming a pouch interior, an upwardly extending flap from a portion of said top edge for at least partially closing off said pouch interior from the exterior environment and leaving a space defined by said flap, said pouch interior and said waistband, said flap having at least two closure mechanisms attachable to and detachable from at least two closure mechanisms disposed on said pouch exterior, said flap extendable over said waistband such that said pouch is suspended from said bottom edge and secured with fastening mechanisms to said waistband, when said at least two flap closure mechanisms and said at least two pouch closure mechanisms are attached, said pouch capable of containing at least one post-surgical fluid drainage collection container;

at least two loop bands, at least one of said at least two loop bands is disposed on said waistband on a first side of one of said plurality of pouches and at least one of said at least two loop bands is disposed on said waistband on a second side of said one of said plurality of pouches, said second side is oppositely disposed from said first side with respect to said one of said plurality of pouches, each of said at least two loop bands includes a bottom edge and a pair of attachable and detachable closure mechanisms located at said loop band bottom edge, said pair of closure mechanisms readily attachable and detachable from said waistband bottom edge;

whereby at least one fluid drainage tube is capable of extending downwardly and channeled through the space into said fluid drainage collection container inside said one of said plurality of pouches, said at least one fluid drainage tube securable between said waistband and at least one of said at least two loop bands when its corresponding loop band closure mechanism is attached to said waistband.

6. The pouch assembly of claim 5, wherein each of said at least two flap closure mechanisms and each of said at least two pouch closure mechanisms comprise cooperating hook and loop fastening material.

7. The pouch assembly of claim 5, wherein each of said at least two flap closure mechanisms and each of said at least two pouch closure mechanisms comprise press-fit fasteners.

8. The pouch assembly of claim 5, wherein each of said at least two flap closure mechanisms and each of said at least two pouch closure mechanisms comprise magnetic fasteners.

* * * * *